(12) United States Patent
McMichael

(10) Patent No.: US 6,383,741 B2
(45) Date of Patent: May 7, 2002

(54) METHOD FOR TREATMENT OF CANINE DISTEMPER

(75) Inventor: John McMichael, Delanson, NY (US)

(73) Assignee: Milkhaus Laboratory, Inc., Delanson, NY (US)

( * ) Notice: Subject to any disclaimer, the term of this patent is extended or adjusted under 35 U.S.C. 154(b) by 0 days.

(21) Appl. No.: 09/747,551

(22) Filed: Dec. 22, 2000

Related U.S. Application Data

(60) Provisional application No. 60/173,378, filed on Dec. 28, 1999.

(51) Int. Cl.$^7$ .................. A16K 39/175; A16K 39/165; A16K 39/12; C12Q 1/70; C12N 15/45
(52) U.S. Cl. ............ 435/5; 424/212.1; 424/205.1; 424/818; 424/213.1; 514/44; 435/69.3; 435/91.33
(58) Field of Search .............. 424/205.1, 818, 424/212.1, 213.1; 514/44; 435/5, 69.3, 91.33

(56) References Cited

U.S. PATENT DOCUMENTS

| | | | | |
|---|---|---|---|---|
| 3,836,648 A | * | 9/1974 | Chang et al. | 424/195 |
| 4,567,043 A | | 1/1986 | Acree et al. | 424/89 |
| 4,824,785 A | | 4/1989 | Acree et al. | 435/237 |
| 5,013,663 A | | 5/1991 | Acree et al. | 435/237 |
| 5,807,840 A | * | 9/1998 | Hirschman | 514/44 |
| 5,911,999 A | | 6/1999 | Bordt et al. | 424/211.1 |
| 6,074,651 A | | 1/2000 | Bordt et al. | 424/211.1 |

* cited by examiner

*Primary Examiner*—Ali R. Salimi
*Assistant Examiner*—Duogun Li
(74) *Attorney, Agent, or Firm*—Marshall, Gerstein & Borun

(57) ABSTRACT

The present invention relates to a treatment for animals having canine distemper by administering a composition comprising an attenuated canine distemper virus a sub-vaccine virus level effective to alleviate symptoms canine distemper. The invention also provides a treatment for animals having canine distemper by administering a composition comprising an attenuated canine measles virus a sub-vaccine virus level effective to alleviate symptoms canine distemper.

5 Claims, No Drawings

METHOD FOR TREATMENT OF CANINE DISTEMPER

This application claims the benefit of U.S. Provisional Patent Application Ser. No. 60/173,378, filed Dec. 28, 1999, the disclosure of which is hereby incorporated by reference.

BACKGROUND OF THE INVENTION

This invention relates generally to the treatment of canine distemper and compositions for use therein.

Canine distemper is a common and often fatal disease of dogs. It is caused by a virus and is spread most often when animals come into contact with the bodily secretions of other animals that are infected with the disease. Over 50% of adult dogs and 80% of puppies who become infected with distemper die. Of those that survive, many will suffer permanent damage to their nervous systems and will suffer from seizures and paralysis for the remainder of their lives.

The symptoms most commonly associated with distemper are red runny eyes and a nasal discharge. Vomiting, diarrhea and fever soon develop, followed by various disorders of the nervous system. Puppies three to six months old are particularly susceptible to the disease.

While vaccination with modified live virus vaccines has been particularly useful in reducing the incidence and spread of the disease, there are currently no drugs available which will cure or treat the symptoms of the disease. As with most viruses, supportive therapy to strengthen and nourish the body and prevent secondary infection remains the only option for animals that contract distemper. When recovery does occur, it is a lengthy process and dogs that survive are left with life-long debilitating conditions. As a result, most veterinarians recommend euthanasia for dogs who develop the disease.

Accordingly, there remains a need for methods of treatment of canine distemper.

SUMMARY OF THE INVENTION

The invention provides methods for treating an animal suffering from canine distemper comprising the step of: administering a composition comprising an attenuated canine distemper virus at a sub-vaccine level effective to alleviate symptoms of canine distemper. A preferred source of attenuated canine distemper virus and of attenuated canine measles virus for use according to the invention is the Vanguard® D-M vaccine (Pfizer) which contains highly attenuated strains of canine distemper virus and measles virus.

The attenuated canine distemper virus and/or attenuated canine measles virus are administered at sub-vaccine levels. Sub-vaccine levels are defined as levels less than those sufficient to induce a protective humoral immune response associated with a prophylactically effective titre of antibodies. According to one aspect of the invention, the composition comprises from about $10^{-3}$ $TCID_{50}$ to about 500 $TCID_{50}$ attenuated canine distemper virus per dose and preferably two or three doses are administered daily. More preferably, the composition is administered at a dosage of about 2 $TCID_{50}$. According to one embodiment of the invention, a 2 $TCID_{50}$ dose may be provided by administration of 0.2 ml of a 1:25 dilution of Vanguard® D-M vaccine (Pfizer). Alternatively according to another aspect of the invention, the composition comprises from about $10^{-3}$ $TCID_{50}$ to about 500 $TCID_{50}$ attenuated canine measles virus per dose and preferably two or three doses are administered daily. More preferably, the composition is administered at a dosage of about 2 $TCID_{50}$.

The compositions of the invention may be administered to animals by a variety of suitable methods with means selected from the group consisting of subcutaneous, intravenous, oral and intramuscular administration being preferred. Particularly preferred methods of administration is the subcutaneous methods of administration. When the composition is administered subcutaneously, it is preferred that two or three doses be administered daily.

According to one preferred method the composition is administered to a animal in a two or three daily dosages of about 0.2 cc in a pharmaceutically acceptable carrier. Such pharmaceutically-acceptable carriers include water, saline, albumin, and dextrose and combinations thereof.

Compositions of the invention for treatment of the symptoms of canine distemper comprise canine distemper attenuated vaccine at a sub-vaccine level effective to alleviate symptoms of canine distemper in a pharmaceutically acceptable carrier. Preferred compositions are those which comprise from about from about $10^{-3}$ $TCID_{50}$ to about 500 $TCID_{50}$ attenuated canine distemper virus per dose with those comprising about 2 $TCID_{50}$ per dose being most preferred. Alternative preferred compositions according to the invention comprise from about $10^{-3}$ $TCID_{50}$ to about 500 $TCID_{50}$ attenuated canine measles virus per dose and preferably two or three doses are administered daily. More preferably, the composition is administered at a dosage of about 2 $TCID_{50}$.

Additional aspects and advantages of the invention will become apparent upon consideration of the following detailed description thereof.

DETAILED DESCRIPTION OF THE INVENTION

The present invention relates to the discovery that the administration of canine distemper attenuated vaccine at a sub-vaccine levels is effective to alleviate symptoms of canine distemper. While not wishing to be bound by a particular theory of invention, it is believed that while the distemper virus certainly induces the disease, the victim's immune response to the virus aggravates the disease. Therefore, by selectively controlling the aberrant response by specific stimulation of a targeted subpopulation of suppressor T cells, the response can be mitigated without compromising the animal's ability to combat the virus and survive. Administration of canine distemper virus according to the invention functions to accomplish this goal. Moreover, because both rubeola (measles virus) and canine distemper virus are from the family paramyxoviridae and the genus morbillivirus they are closely related and administration of rubeola in subvaccine levels has been found to alleviate the symptoms of canine distemper virus infection.

The following Example illustrates a preferred embodiment of the invention and provides evidence of the effectiveness of claimed treatment methods. Numerous improvements and further aspects of the invention are apparent to the skilled artisan upon consideration of the Example which follows.

EXAMPLE

According to this example, twelve dogs suffering from canine distemper and exhibiting symptoms of lethargy, anorexia, central nervous system disorders and respiratory disorders were treated according to the methods of the invention. Specifically, the dogs were treated by subcutaneous injection two or three times daily with 0.2 cc of a 1:25 dilution of a commercially available distemper virus vaccine (Vanguard® D-M vaccine, Pfizer) The diluted composition comprises about 2 $TCID_{50}$. The symptoms of eleven of the twelve dogs resolved within 24 to 48 hours and there were no long term symptoms in any of the recovered dogs.

Positive results similar to those reported in the Example were found when canine measles (rubeola) virus was administered to dogs suffering from distemper in amounts of about 2 $TCID_{50}$.

The invention has been described in terms of its preferred embodiments and is only intended to be limited by the scope of the following claims.

What is claimed:

1. A method for treating an animal suffering from canine distemper comprising the step of:

administering a composition comprising an attenuated canine distemper virus at a sub-vaccine level effective to alleviate symptoms of canine distemper, wherein the sub-vaccine levels comprises about 2 $TCID_{50}$ attenuated canine distemper virus per 2. The method of claim 1 wherein said composition is administered to an animal in a single dose in about 0.2 cc in a pharmaceutically acceptable carrier.

3. The method of claim 1 wherein multiple daily doses of said composition are administered to the animal.

4. The method of claim 1 wherein the composition is administered to an animal from the group consisting of subcutaneously, intravenously or intramuscularly.

5. The method of claim 4 wherein the composition is administered to an animal subcutaneously.

* * * * *

UNITED STATES PATENT AND TRADEMARK OFFICE
CERTIFICATE OF CORRECTION

PATENT NO.     : 6,383,741 B2
DATED          : May 7, 2002
INVENTOR(S)    : McMichael It is certified that error appears in the above-identified patent and that said Letters Patent is hereby corrected as shown below:

Column 4,
Lines 4-5, please delete "sub-vaccine levels comprises about 2 $TCID_{50}$ attenuated canine distemper virus per" and insert in its place -- sub-vaccine levels comprise about 2 $TCID_{50}$ attenuated canine distemper virus per dose --.
Line 9, please delete "wherein" and insert in its place -- where --.

Signed and Sealed this

Twenty-fourth Day of September, 2002

Attest:

JAMES E. ROGAN
Attesting Officer
Director of the United States Patent and Trademark Office